United States Patent [19]
Hwang

[11] Patent Number: 5,941,824
[45] Date of Patent: Aug. 24, 1999

[54] ULTRASONIC DIAGNOSTIC APPARATUS HAVING A PATIENT-USE MONITOR

[75] Inventor: Jae-Sub Hwang, Seoul, Rep. of Korea

[73] Assignee: Samsung Electronics Co., Ltd., Rep. of Korea

[21] Appl. No.: 09/018,009

[22] Filed: Feb. 3, 1998

[30] Foreign Application Priority Data

Feb. 4, 1997 [KR] Rep. of Korea ........................ 97-3421

[51] Int. Cl.⁶ ................................................. A61B 08/00
[52] U.S. Cl. ............................................................. 600/437
[58] Field of Search ..................................... 600/437, 438, 600/439; 382/132

[56] References Cited

U.S. PATENT DOCUMENTS 5,129,397  7/1992  Jingu et al. .............................. 600/437
5,757,952  5/1998  Bytaert et al. .......................... 382/132
5,851,186 12/1998  Wood et al. ............................. 600/437

*Primary Examiner*—Francis J. Jaworski
*Assistant Examiner*—Maulin Patel
*Attorney, Agent, or Firm*—Dilworth & Barrese

[57] ABSTRACT

An ultrasonic diagnostic apparatus uses an ultrasonic wave to obtain information on the inner state of a human body without conducting a surgical operation on the patient. The ultrasonic diagnostic apparatus includes a receiving recess so that a patient-use monitor can be connected with and disconnected from a main body. Diagnostic results measured in the main body are displayed on the patient-use monitor including a support shaft which can be inserted into the receiving recess. Thus, the patient can see his or her diagnostic results easily. Since the patient-use monitor is compatible with other types of ultrasonic diagnostic apparatuses having each receiving recess installed in the main body, the patient-use monitor can be used in other types of the ultrasonic diagnostic apparatuses.

8 Claims, 2 Drawing Sheets

ULTRASONIC DIAGNOSTIC APPARATUS HAVING A PATIENT-USE MONITOR

BACKGROUND OF THE INVENTION

The present invention relates to an ultrasonic diagnostic apparatus, and more particularly, to an ultrasonic diagnostic apparatus having a patient-use monitor mounted at the side of a body of the ultrasonic diagnostic apparatus, in order to make a patient see his or her diagnostic results easily.

In general, an ultrasonic diagnostic apparatus uses an ultrasonic wave to obtain information on the inner state of a human body without having a surgical operation with respect to the patient. The ultrasonic diagnostic apparatus emits an ultrasonic wave into a human body, analyzes a reflected wave from the human body, and displays information on the human body on a monitor. A monitor for displaying human body information thereon is positioned in front of an operator in order to have the operator facilitate to watch the monitor. As a result, the patient cannot see his or her diagnostic results during the operator's diagnosis. In the case where the patient wishes to see his or her diagnostic results, the operator should turn the monitor to the direction of the patient's visibility. As an alternative for enabling a patient to see his or her diagnostic results, there is a method for installing a subsidiary monitor in the visible area in which the patient can see it in addition to a main monitor for enabling an operator to monitor the human body of the patient.

However, a support for supporting a subsidiary monitor is needed to install the subsidiary monitor in addition to a main monitor placed on top of the main body of the ultrasonic diagnostic apparatus. Thus, such a support requires a more space for supporting a monitor, and movement of the subsidiary monitor inconveniences an operator.

SUMMARY OF THE INVENTION

To solve the above problems, it is an object of the present invention to provide an ultrasonic diagnostic apparatus which is compatible with other types of ultrasonic diagnostic apparatuses, in which a compact subsidiary monitor for a patient's use which is constructed as a liquid crystal panel is detachably installed in any part of the main body.

To accomplish the above object of the present invention, there is provided an ultrasonic diagnostic apparatus including a main body in which a conversion circuit for converting an ultrasonic echo signal received from a probe into a video signal is installed, and a main monitor for displaying the video signal thereon, the ultrasonic diagnostic apparatus comprising:

a receiving recess formed at the main body, for housing a patient-use monitor; and a patient-use monitor including a support shaft which is connected with and disconnected from the receiving recess, and a display for displaying a video signal applied from the main body.

BRIEF DESCRIPTION OF THE DRAWINGS

The preferred embodiment is described with reference to the drawings wherein.

DETAILED DESCRIPTION OF THE PREFERRED EMBODIMENT

A preferred embodiment of the present invention will be described in detail with reference to the accompanying drawings.

Figure 1:
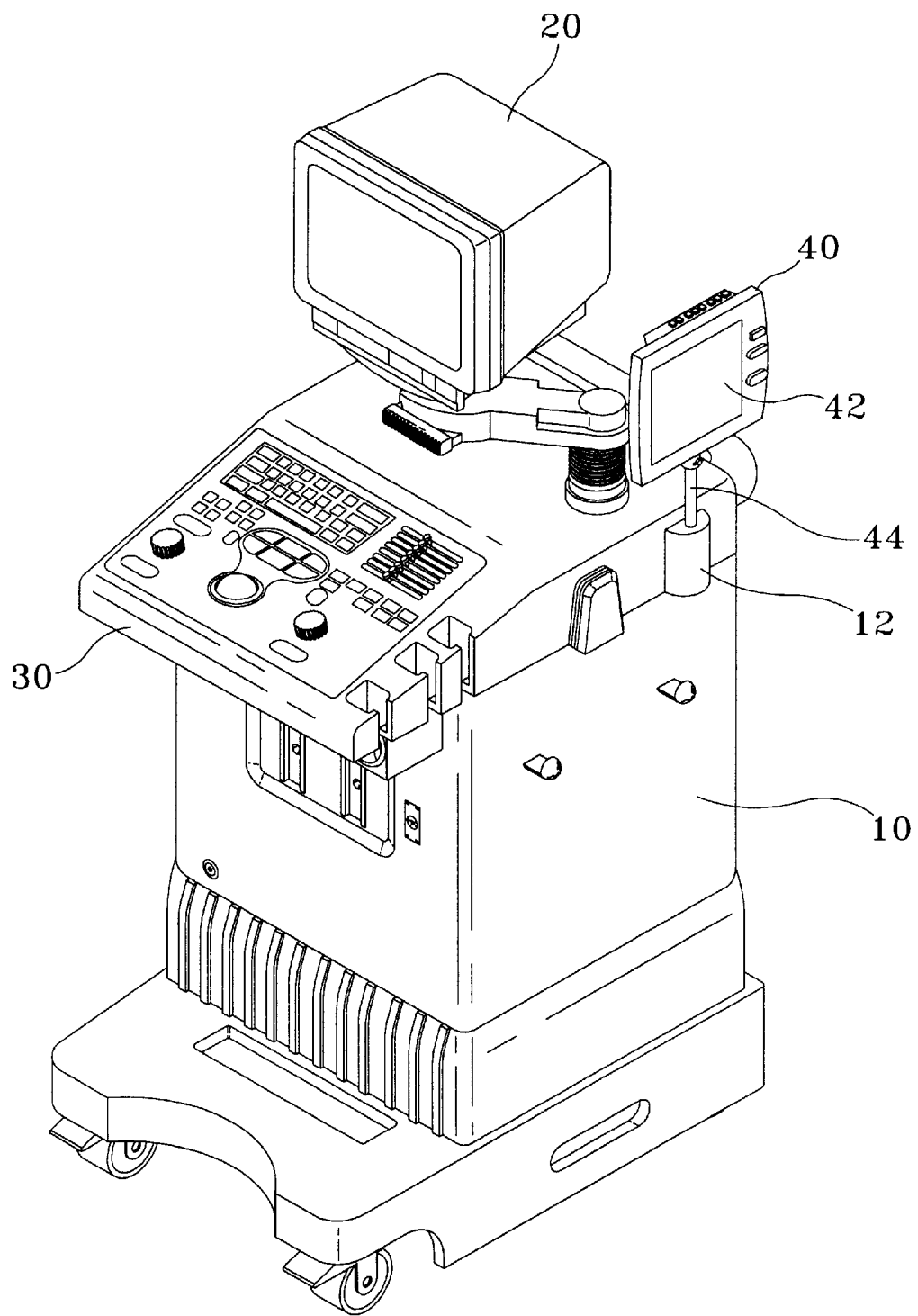
FIG. 1 is a perspective view of an ultrasonic diagnostic apparatus having a patient-use monitor according to a preferred embodiment of the present invention.
Figure 2:
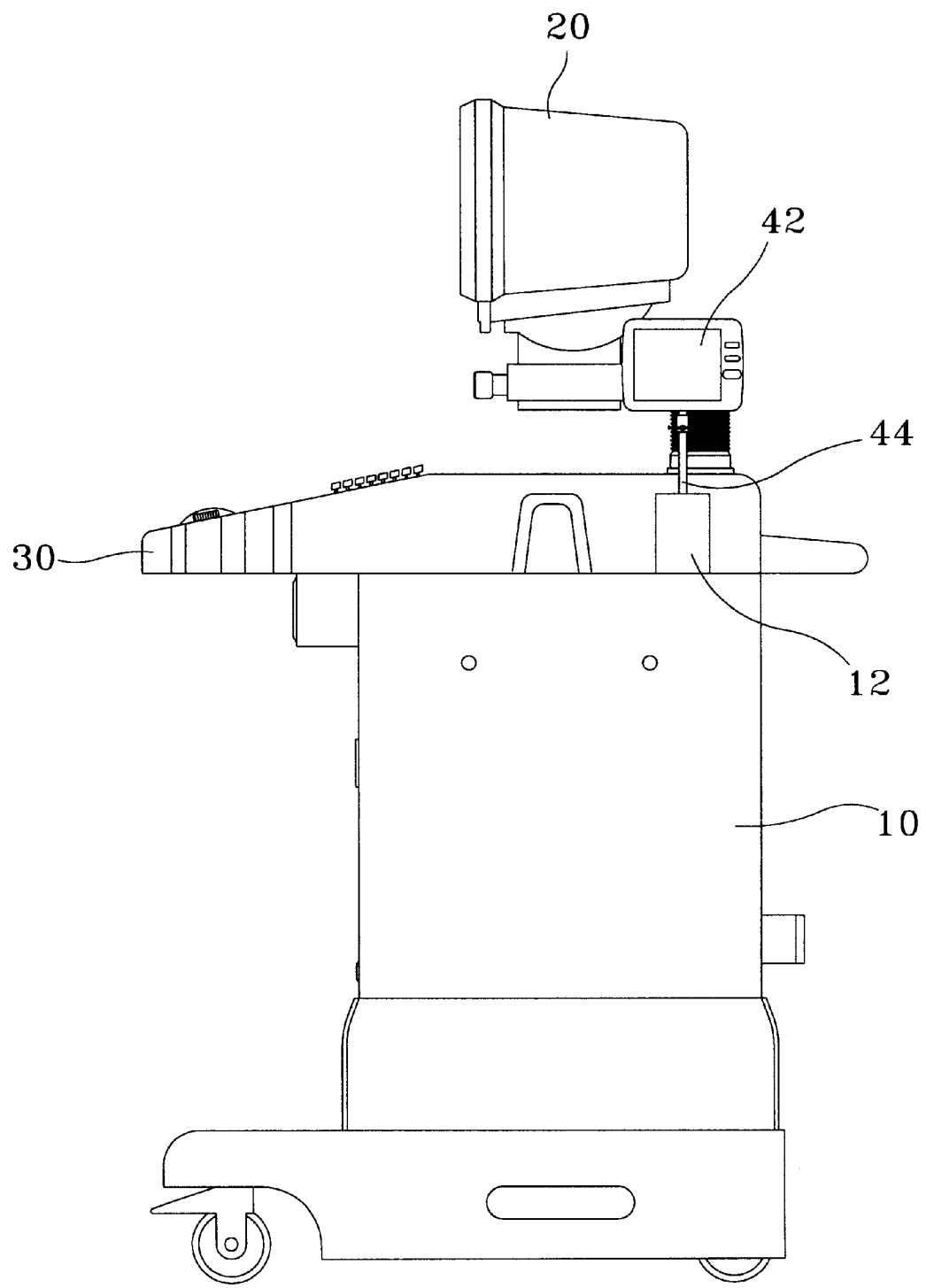
FIG. 2 is a side view of the apparatus shown in FIG. 1.

In FIGS. 1 and 2 showing an ultrasonic diagnostic apparatus having a patient-use monitor according to a preferred embodiment of the present invention, the ultrasonic diagnostic apparatus includes a main body 10 housing therein a circuit for converting an ultrasonic echo signal input from a probe (not shown) into a video signal to be displayed, and a main monitor 20 for displaying the video signal thereon. The main monitor 20 is connected to the main body 10, and usually placed in front of an operator in order to enable the operator to monitor the state of a patient. The main monitor 20 can be rotated so that the operator can see diagnostic results at various angles of view. A key manipulator board 30 needed for diagnosis is located on the top-front of the main body 10. A receiving recess 12 for a patient-use monitor 40 is formed at the side of the main body 10. Since the patient is usually located at the side of the ultrasonic diagnostic apparatus, it is preferable that the receiving recess 12 to be connected with/disconnected from the patient-use monitor 40 is formed at the side of the main body 10. The patient-use monitor 40 according to the present invention includes a display 42 for displaying an image applied from the main body 10 and a rod-shaped support shaft 44 which is inserted into the receiving recess 12 of the main body 10.

In this embodiment of the present invention, a compact liquid crystal monitor can be used as the display 42. The patient-use monitor 40 includes a video signal input port (not shown) for receiving a video signal applied from the main body 10. The main body 10 and the video signal input port are connected to each other via a predetermined video signal transmission cable. Also, the patient-use monitor 40 includes a power input port (not shown) via which power is supplied from the main body 10. Otherwise, power can be supplied to the patient-use monitor 40 via an adapter connector from an external source. Also, the display 42 can be rotated around the fixed support shaft 44.

The ultrasonic diagnostic apparatus according to the present invention is compatible with other types of ultrasonic diagnostic apparatuses including each receiving recess 12 for housing a support shaft 44 of a patient-use monitor 40. Thus, the video signals applied from other types of the ultrasonic diagnostic apparatuses can be displayed on the patient-use monitor 40. Also, the patient-use monitor 40 can use other kinds of monitors as well as the above-described liquid crystal monitor. It is also more preferable that the patient-use monitor 40 can be easily moved and is compact and light.

As described above, the ultrasonic diagnostic apparatus according to the present invention provides an ultrasonic diagnostic apparatus having a patient-use monitor which is detachable from a main body and enables a patient to see the diagnostic results easily. Since the patient-use monitor of the present invention can be connected with and disconnected from the other types of ultrasonic diagnostic apparatuses having each receiving recess formed on the main body, the patient-use monitor can be used by being connected with other types of the ultrasonic diagnostic apparatuses.

While only certain embodiments of the invention have been specifically described herein, it will be apparent that numerous modifications may be made thereto without departing from the spirit and scope of the invention.

What is claimed is:

1. An ultrasonic diagnostic apparatus including a main body in which a conversion circuit for converting an ultrasonic echo signal received from a probe into a video signal is installed, and a main monitor for displaying the video signal thereon, the ultrasonic diagnostic apparatus comprising:

a receiving recess formed at the main body, for housing a patient-use monitor; and a patient-use monitor including a support shaft which is connected with and adapted to readily disconnectable from the receiving recess, and a display for displaying a video signal applied from the main body.

2. The ultrasonic diagnostic apparatus according to claim 1, wherein said display in the patient-use monitor is a liquid crystal panel.

3. The ultrasonic diagnostic apparatus according to claim 1, wherein said patient-use monitor comprises a power input port receiving power supplied from the main body.

4. The ultrasonic diagnostic apparatus according to claim 3, wherein said patient-use monitor further comprises an external power input port to which power can be supplied from an external source.

5. The ultrasonic diagnostic apparatus according to claim 1, wherein said patient-use monitor comprises a video signal input port receiving a video signal applied from the main body via a predetermined video signal transmission cable.

6. The ultrasonic diagnostic apparatus according to claim 1, wherein said support shaft is a fixed support shaft and said display is adapted to be rotated around the fixed support shaft.

7. The ultrasonic diagnostic apparatus according to claim 1, wherein said patient-use monitor is adapted for the use with other types of ultrasonic diagnostic apparatuses having said receiving recess.

8. The ultrasonic diagnostic apparatus according to claim 1, wherein said main body has a side and said patient-use monitor is installed at the side of the main body.

* * * * *

UNITED STATES PATENT AND TRADEMARK OFFICE
CERTIFICATE OF CORRECTION

PATENT NO.    : 5,941,824
DATED         : August 24, 1999
INVENTOR(S)   : Jae-Sub Hwang It is certified that error appears in the above-identified patent and that said Letters Patent is hereby corrected as shown below:

<u>Title page,</u>
Item [73] should read:
"[73] Assignee: Medison Co., Ltd., Republic of Korea".

Signed and Sealed this

Fourteenth Day of August, 2001

Attest:

NICHOLAS P. GODICI
Attesting Officer    Acting Director of the United States Patent and Trademark Office